(12) United States Patent  (10) Patent No.: US 7,437,266 B2
Ueno et al.  (45) Date of Patent: Oct. 14, 2008

(54) TIME-SERIES DATA ANALYZING APPARATUS

(75) Inventors: Ken Ueno, Kawasaki (JP); Ryohei Orihara, Tokyo (JP); Youichi Kitahara, Fuchu (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 228 days.

(21) Appl. No.: 11/390,164

(22) Filed: Mar. 28, 2006

(65) Prior Publication Data

US 2007/0079195 A1  Apr. 5, 2007

(30) Foreign Application Priority Data

Aug. 31, 2005  (JP) ............................. 2005-252108

(51) Int. Cl.
  *G06F 15/00* (2006.01)
(52) U.S. Cl. ..................................... 702/176
(58) Field of Classification Search ................ 702/176, 702/179, 181, 182, 183, 187; 707/6, 7; 700/90; 714/731
  See application file for complete search history.

(56) References Cited

U.S. PATENT DOCUMENTS

2006/0129554 A1* 6/2006 Suyama et al. ................. 707/6
2006/0271533 A1* 11/2006 Sakurai et al. ................. 707/5

FOREIGN PATENT DOCUMENTS

| JP | 10-198750 | 7/1998 |
| JP | 2004-21854 | 1/2004 |
| JP | 2004-348432 | 12/2004 |

OTHER PUBLICATIONS

Rakesh Agrawal, et al., "Mining Sequential Patterns," Proceedings of the 11th International Conference on Data Engineering, pp. 3-14 (1995).

* cited by examiner

*Primary Examiner*—Bryan Bui
(74) *Attorney, Agent, or Firm*—Finnegan, Henderson, Farabow, Garrett & Dunner, L.L.P.

(57) ABSTRACT

A time-series data analyzing apparatus which extracts a composite factor time-series pattern from time-series data. The apparatus includes a dividing device which divides the time-series data into pattern generation time-series data and pattern inspection time-series data which do not include pattern generation time-series data. A first generating device generates a transitional pattern including a support time data indicating a transition of support time and having a transition occurrence probability higher than a minimum occurrence probability in the pattern generation time-series data. A second generating device generates frequently appearing integrated transitional patterns. A second computing device computes cause-and-effect strength of each of the frequently appearing integrated transitional patterns using the pattern inspection time-series data. A display device displays the composite factor time-series pattern having the cause-and-effect strength higher than the minimum cause-and-effect strength given preliminarily.

16 Claims, 21 Drawing Sheets

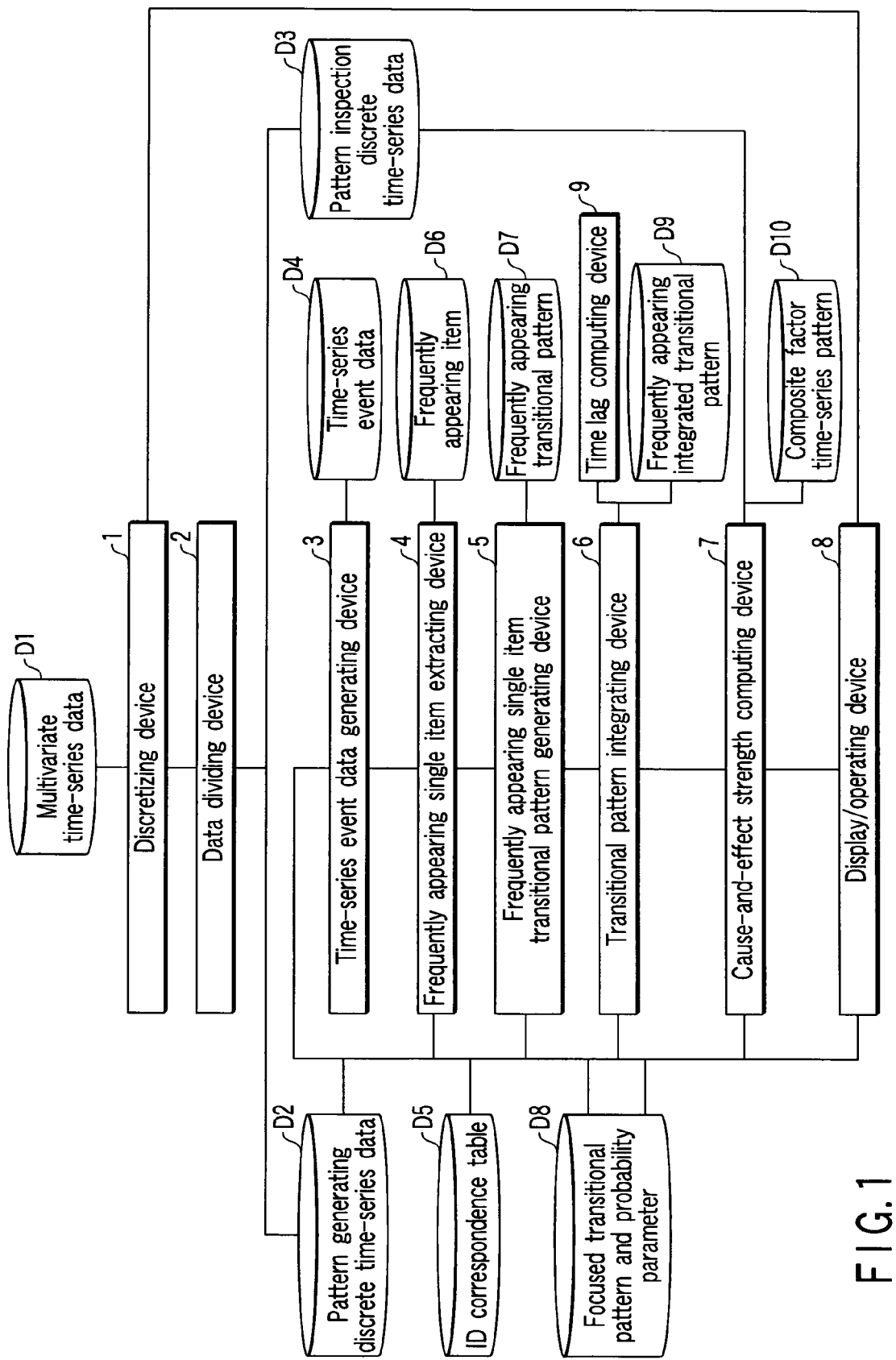
F I G. 1

FIG. 2

| Blood pressure check standard | |
|---|---|
| G | ≤ 120 |
| Y | > 120 and ≤ 130 |
| R | > 130 |

| Examination year | Examined person ID | Blood pressure at time of contraction | Dietary risk | Alcoholism risk |
|---|---|---|---|---|
| 2001 | 1 | 122 | Y | Y |
| 2002 | 1 | 110 | R | R |
| 2003 | 1 | 135 | R | R |
| 2004 | 1 | 150 | G | R |
| 2001 | 2 | 100 | Y | R |
| 2002 | 2 | 110 | Y | Y |
| 2003 | 2 | 141 | R | R |
| 2004 | 2 | 131 | Y | R |
| 2001 | 3 | 134 | Y | Y |
| 2002 | 3 | 160 | R | R |
| 2003 | 3 | 136 | Y | R |
| 2004 | 3 | 145 | R | G |

FIG. 3

| Examination year | Examined person ID | Blood pressure at time of contraction | Dietary risk | Alcoholism risk |
|---|---|---|---|---|
| 2001 | 1 | G | Y | Y |
| 2002 | 1 | G | R | R |
| 2003 | 1 | Y | R | R |
| 2004 | 1 | R | G | R |
| 2001 | 2 | G | Y | R |
| 2002 | 2 | Y | Y | Y |
| 2003 | 2 | R | R | R |
| 2004 | 2 | Y | Y | R |
| 2001 | 3 | Y | Y | Y |
| 2002 | 3 | R | R | R |
| 2003 | 3 | Y | Y | R |
| 2004 | 3 | R | R | G |

FIG. 4

Minimum occurrence probability = 0.5 p(Blood pressure check_G)=2/3
p(Blood pressure check_Y)=3/3
p(Blood pressure check_R)=3/3

| p(Dietary risk_G)=1/3 | Blood pressure check_G |
| p(Dietary risk_Y)=3/3 | Blood pressure check_Y |
| p(Dietary risk_R)=3/3 | Blood pressure check_R |
| | Dietary risk_Y |
| p(Alcoholism risk_G)=1/3 | Dietary risk_R |
| p(Alcoholism risk_Y)=3/3 | Alcoholism risk_Y |
| p(Alcoholism risk_R)=3/3 | Alcoholism risk_R |
| Computation of probability | Extracted items (set of frequently appearing items) |

FIG. 7

| Worsened | Corresponding examined person ID |
|---|---|
| p(Blood pressure check_G→Blood pressure check_Y)=66.7% | 1,2 |
| p(Blood pressure check_G→Blood pressure check_R)=66.7% | 1,2 |
| p(Blood pressure check_Y→Blood pressure check_R)=100% | 1,2,3 |
| No change | |
| p(Blood pressure check_G→Blood pressure check_G)=33.3% | 1 |
| p(Blood pressure check_Y→Blood pressure check_Y)=33.3% | 2 |
| p(Blood pressure check_R→Blood pressure check_R)=33.3% | 3 |
| Improved | |
| p(Blood pressure check_Y→Blood pressure check_G)=0% | |
| p(Blood pressure check_R→Blood pressure check_G)=0% | |
| p(Blood pressure check_R→Blood pressure check_Y)=66.7% | 2,3 |

FIG. 9

| Worsened | Corresponding examined person ID |
|---|---|
| p(Dietary risk_Y→Dietary risk_R)=100% | 1,2,3 |
| No change | |
| p(Dietary risk_Y→Dietary risk_Y)=66.7% | 2,3 |
| p(Dietary risk_R→Dietary risk_R)=66.7% | 1,3 |
| Improved | |
| p(Dietary risk_R→Dietary risk_Y)=66.7% | 2,3 |

FIG. 10

| Worsened | Corresponding examined person ID |
|---|---|
| p(Alcoholism risk_Y→Alcoholic risk_R)=100% | 1,2,3 |
| No change | |
| p(Alcoholism risk_Y→Alcoholic risk_Y)=0% | |
| p(Alcoholism risk_R→Alcoholic risk_R)=100% | 1,2,3 |
| Improved | |
| p(Alcoholism risk_R→Alcoholic risk_Y)=33.3% | 1 |

FIG. 11

| | Corresponding examined person ID |
|---|---|
| Worsened | |
| Blood pressure check_G→Blood pressure check_Y | 1,2 |
| Blood pressure check_G→Blood pressure check_R | 1,2 |
| Blood pressure check_Y→Blood pressure check_R | 1,2,3 |
| Dietary risk_Y→Dietary risk_R | 1,2,3 |
| Alcoholism risk_Y→Alcoholism risk_R | 1,2,3 |
| Improved | |
| Blood pressure check_R→Blood pressure check_Y | 2,3 |
| Dietary risk_R→Dietary risk_Y | 2,3 |
| No change | |
| Dietary risk_Y→Dietary risk_Y | 2,3 |
| Dietary risk_R→Dietary risk_R | 1,3 |
| Alcoholism risk_R→Alcoholism risk_R | 1,2,3 |

FIG. 12

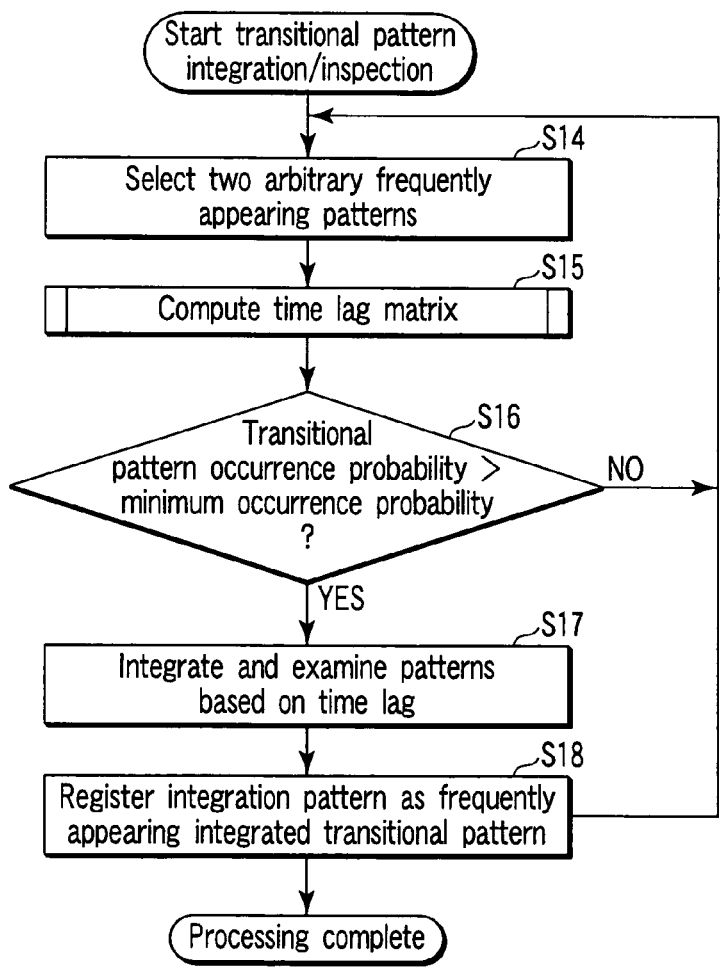

FIG. 13

Blood pressure check_G→Blood pressure check_Y:
  ID    Support time data
  1     2002→2003
  2     2001→2002, 2001→2004

Blood pressure check_G→Blood pressure check_R:
  ID    Support time data
  1     2002→2004
  2     2001→2003

Blood pressure check_Y→Blood pressure check_R:
  ID    Support time data
  1     2003→2004
  2     2002→2003
  3     2001→2002, 2003→2004, 2001→2004

Blood pressure check_R→Blood pressure check_Y:
  ID    Support time data
  2     2003→2004
  3     2002→2003

F I G. 15

Dietary risk_Y→Dietary risk_R:
  ID    Support time data
  1     2001→2002, 2001→2003
  2     2001→2003, 2002→2003
  3     2001→2002, 2003→2004, 2001→2004

Dietary risk_R→Dietary risk_Y:
  ID    Support time data
  2     2003→2004
  3     2002→2003

Dietary risk_Y→Dietary risk_Y:
  ID    Support time data
  2     2001→2002, 2001→2004
  3     2001→2003

Dietary risk_R→Dietary risk_R:
  ID    Support time data
  1     2002→2003
  3     2002→2004

F I G. 16

Alcoholism risk_Y→Alcoholism risk_R :
    ID      Support time data
    1       2001→2002, 2001→2003, 2001→2004
    2       2002→2003, 2002→2004
    3       2001→2002, 2001→2003

Alcoholism risk_R→Alcoholism risk_R :
    ID      Support time data
    1       2002→2003, 2002→2004, 2003→2004
    2       2001→2003, 2001→2004, 2003→2004
    3       2002→2003

FIG. 17

Dietary risk_Y→Dietary risk_R           Dietary risk_Y→Dietary risk_R
    ID      MIN (Support time)              ID      MAX (Support time)
    1       2001, 2001, 2001                1       2002, 2003, 2004
    2       2002, 2002                      2       2003, 2004
    3       2001, 2001                      3       2002, 2003

Dietary risk_Y→Dietary risk_R
                  ID      MAX-MIN-1
                  1       0, 1, 2
                  2       0, 1
                  3       0, 1              2 max

FIG. 18

Time Lags for Ending Year (unit : year)

| Time Lags for Start Year (unit : year) | −2 | −1 | ±0 | +1 | +2 |
|---|---|---|---|---|---|
| −2 | | | | | |
| −1 | | | | | |
| ±0 | | | | | |
| +1 | | | | | |
| +2 | | | | | |

FIG. 19

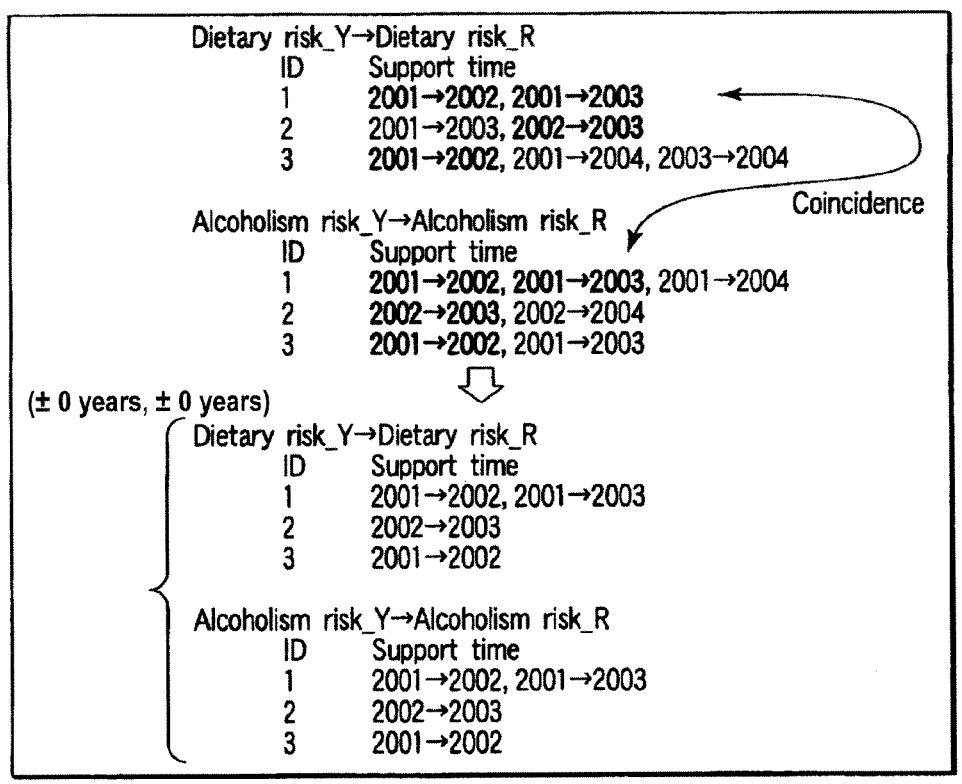
F I G. 20

Dietary risk_Y→Dietary risk_R
Integration
Alcoholism risk_R→Alcoholism risk_R

| | | Time Lags for Ending Year (unit : year) | | | | |
|---|---|---|---|---|---|---|
| | | −2 | −1 | ±0 | +1 | +2 |
| Time Lags for Start Year (unit : year) | −2 | 0% | 0% | 0% | 0% | 0% |
| | −1 | 0% | 0% | 33.3% | 33.3% | 0% |
| | ±0 | 0% | 0% | 33.3% | 33.3% | 0% |
| | +1 | 0% | 33.3% | 33.3% | 100.0% | 0% |
| | +2 | 0% | 0% | 0% | 33.3% | 0% |

Blood pressure check_Y→Blood pressure check_R
Support time
ID
1  2003→2004
2  2002→2003
3  2001→2002, 2003→2004, 2001→2004

Dietary risk_Y→Dietary risk_R
Support time
ID
1  2001→2002, 2001→2003
2  2002→2003
3  2001→2002

Alcoholism risk_Y→Alcoholism risk_R
Support time
ID
1  2001→2002, 2001→2003
2  2002→2003
3  2001→2002

(± 0 years, ± 0 years)

Time Lags for Ending Year (unit : year)

| Time Lags for Start Year (unit : year) | -2 | -1 | ±0 | +1 | +2 |
|---|---|---|---|---|---|
| -2 | 66.7% | 0% | 0% | 0% | 0% |
| -1 | 0% | 0% | 0% | 0% | 0% |
| ±0 | 0% | 0% | 66.7% | 0% | 0% |
| +1 | 0% | 0% | 0% | 0% | 0% |
| +2 | 0% | 0% | 0% | 0% | 0% |

Time lags in which (± 0 years, ± 0 years) and (-2 years, -2 years) frequently appear

F I G. 26

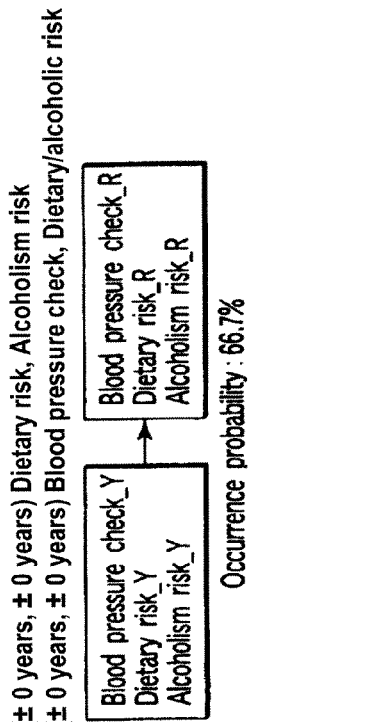
F I G. 27
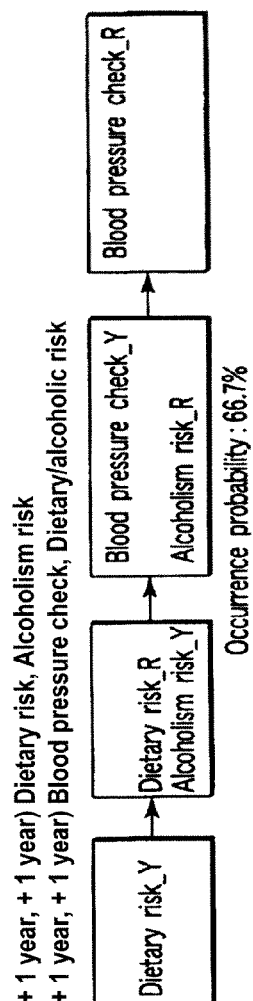
F I G. 28
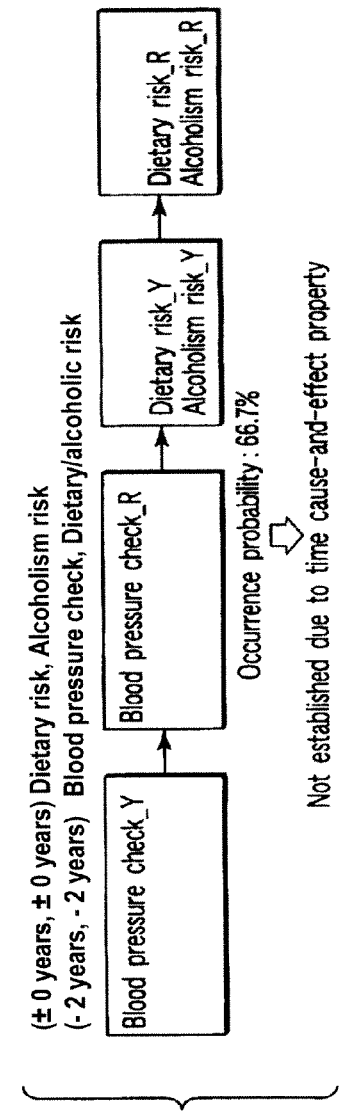
F I G. 29

| Examination year | Examined person ID | Blood pressure check | Dietary risk | Alcoholism risk |
|---|---|---|---|---|
| 2001 | 4 | G | Y | G |
| 2002 | 4 | G | R | R |
| 2003 | 4 | Y | R | R |
| 2004 | 4 | R | G | R |
| 2001 | 5 | G | Y | R |
| 2002 | 5 | Y | Y | Y |
| 2003 | 5 | R | R | R |
| 2004 | 5 | Y | Y | Y |
| 2001 | 6 | Y | Y | Y |
| 2002 | 6 | R | R | R |
| 2003 | 6 | Y | Y | R |
| 2004 | 6 | R | R | R |
F I G. 31
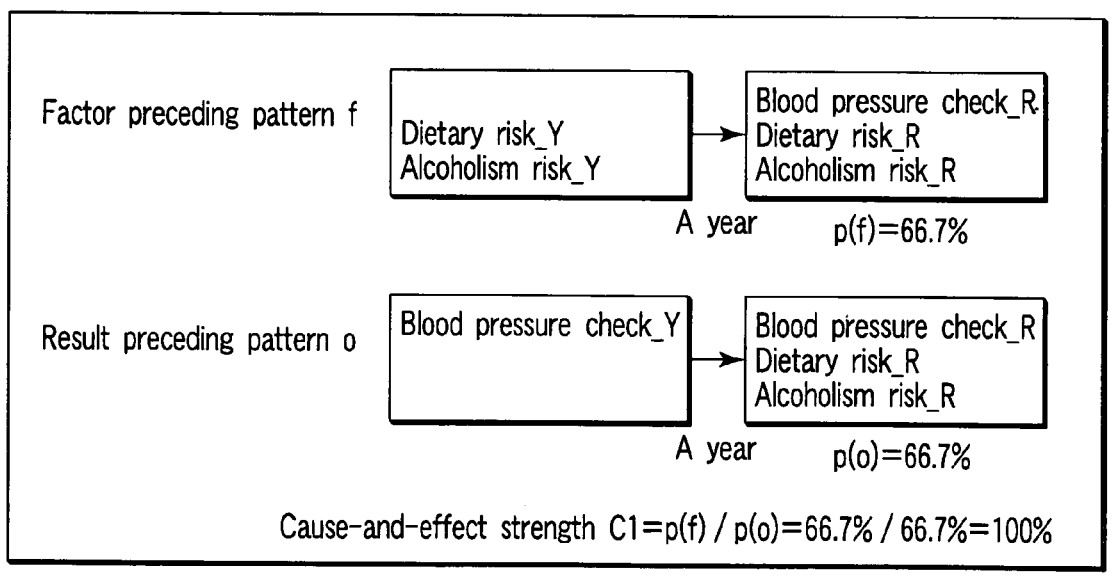
F I G. 32

TIME-SERIES DATA ANALYZING APPARATUS

CROSS-REFERENCE TO RELATED APPLICATIONS

This application is based upon and claims the benefit of priority from prior Japanese Patent Application No. 2005-252108, filed Aug. 31, 2005, the entire contents of which are incorporated herein by reference.

BACKGROUND OF THE INVENTION

1. Field of the Invention

The present invention relates to a time-series data analyzing apparatus, time-series data analyzing method and time-series data analyzing program for analyzing multivariate time series data.

2. Description of the Related Art

Typical methods for analyzing data taking into account composite factor include covariance analysis (ANCOVA), covariance structure analysis, hidden Markov model (HMM) and the like. However, methods such as the covariance analysis method require strict prerequisites such as normality of distribution and parallelism of regression line of each factor; and the hidden Markov model method and the like require an analyzer to consider dependency relationship carefully before analysis. Therefore, if there is no way for finding out what composite factor has occurred, it is difficult to analyze what structure the composite factor has. For these reasons, it is considered difficult to take out a composite transitional pattern from a large amount of data or complicated data without a hypothetical basis.

"Disease Condition Control Method and System" of Jpn. Pat. Appln. KOKAI No. 10-198750 has disclosed a method for obtaining associated rule for discriminating a patient in a critical condition using his disease history and disease intervention history. However, this method is constructed to determine a patient to be intervened and it is considered difficult to pick out only the related composite factor.

Although "Health Control Assistant System" of Jpn. Pat. Appln. KOKAI No. 2004-348432 has disclosed a system intended for improvement of lifestyle habits based on doctor inquiry items for prevention or improvement of lifestyle disease, this system does not aim at the time-series analysis using inspection values and doctor inquiry data.

"Health Instruction Assistant System, Server, Client Terminal and Health Instruction Assistant Program" of Jpn. Pat. Appln. KOKAI No. 2004-21854 has disclosed a system for assisting instruction about lifestyle habits such as diet control and physical exercise to chronic disease patients in medical institutions. This system presents user an advice about improvement of blood pressure and other items depending on his or her symptom from replies of diagnostic table including inspection values and doctor inquiry. Although this Jpn. Pat. Appln. KOKAI No. 2004-21854 has described about a trend graph in which time-series values are plotted, it has described nothing about finding out a composite factor from the time-series data.

BRIEF SUMMARY OF THE INVENTION

One aspect of the present invention is directed to a time-series data analyzing apparatus which extracts a composite factor time-series pattern from time-series data. The apparatus includes a dividing device which divides the time-series data into pattern generation time-series data and pattern inspection time-series data which do not include pattern generation time-series data. A first generating device generates a transitional pattern including a support time data indicating a transition of support time and having a transition occurrence probability higher than a minimum occurrence probability in the pattern generation time-series data. A second generating device generates frequently appearing integrated transitional patterns. A second computing device computes cause-and-effect strength of each of the frequently appearing integrated transitional patterns using the pattern inspection time-series data. A display device displays the composite factor time-series pattern having the cause-and-effect strength higher than the minimum cause-and-effect strength given preliminarily.

BRIEF DESCRIPTION OF THE SEVERAL VIEWS OF THE DRAWING

FIG. 1 is a block diagram showing a time-series data analyzing apparatus according to an embodiment of the present invention;

FIG. 2 is a diagram showing an example of blood pressure check standards;

FIG. 3 is a diagram showing an example of multivariate time-series data;

FIG. 4 is a diagram showing an example of discrete time-series data;

FIG. 7 is a diagram showing an example of frequently appearing single item extraction;

FIG. 9 is a diagram showing an example (blood pressure check) of transitional pattern candidate generation;

FIG. 10 is a diagram showing an example (dietary risk) of the transitional pattern candidate generation;

FIG. 11 is a diagram showing an example (alcoholism risk) of the transitional pattern candidate generation;

FIG. 12 is a diagram showing a frequently appearing transitional pattern;

FIG. 13 is a flowchart showing the processing steps of a transitional pattern integrating device;

FIG. 15 is a diagram showing support time data of the frequently appearing transitional pattern in blood pressure check;

FIG. 16 is a diagram showing support time data of the frequently appearing transitional pattern in dietary risk;

FIG. 17 is a diagram showing support time data of the frequently appearing transitional pattern in alcoholism risk;

FIG. 18 is a diagram showing a specific example of time lag range computation;

FIG. 19 is a diagram showing time lag matrix format obtained by computation;

FIG. 20 is a diagram showing an example 1-1 of pattern integration considering time lag;

FIG. 26 is a diagram showing an example of integration of the frequently appearing integration pattern of dietary/alcoholism risks and the frequently appearing transitional pattern of the blood pressure;

FIG. 27 is a diagram showing an example 1 of an integrated pattern;

FIG. 28 is a diagram showing an example 2 of the integrated pattern;

FIG. 29 is a diagram showing a pattern which cannot be integrated;

FIG. 31 is a diagram showing an example of time-series data for pattern inspection;

FIG. 32 is a diagram showing an example of computation of the cause-and-effect strength;

DETAILED DESCRIPTION OF THE INVENTION

Figure 5:
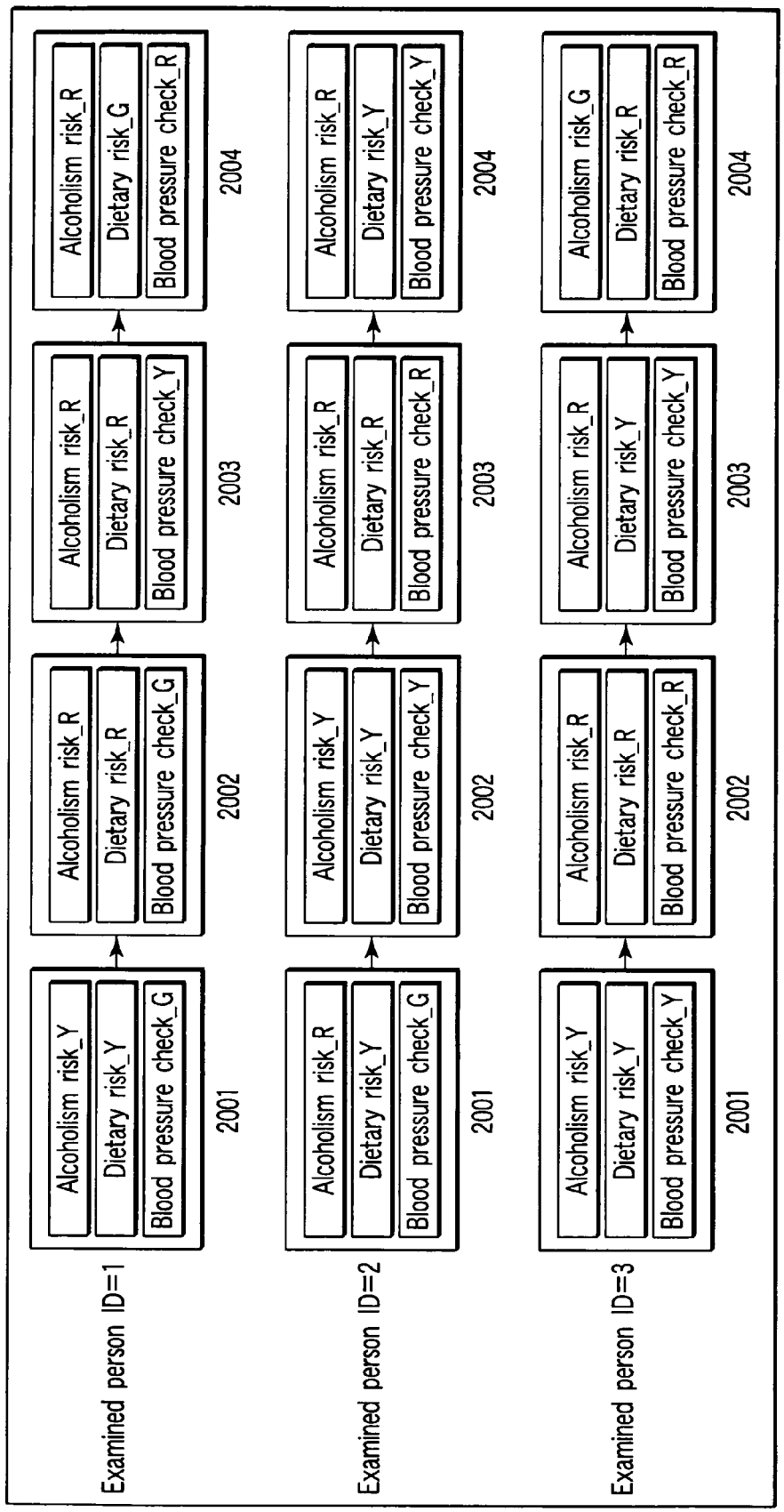
FIG. 5 is a diagram showing an example of time-series event data.

Hereinafter, embodiments of the present invention will be described with reference to the accompanying drawings.

First Embodiment

FIG. 1 is a block diagram showing a time-series data analyzing apparatus according to a first embodiment of the present invention. This apparatus is an apparatus which extracts composite factor time-series pattern indicating the composite factor of focused transitional pattern form multivariate time-series data, and its functional modules include a discretizing device 1, a data dividing device 2, a time-series event data generating device 3, a frequently appearing single item extracting device 4, a frequently appearing single item transitional pattern generating device 5, a time lag computing device 9, a transitional pattern integrating device 6, a cause and effect strength computing device 7, and a display/operation device 8. An embodiment of the present invention may be a program which makes a computer function as a time-series data analyzing apparatus having the components described above. In this case, the program of the embodiment is stored in a program storage device in the computer. The program storage device includes, for example, a nonvolatile semiconductor storage device, a magnetic disk unit or the like. The aforementioned program is read into a random access memory (RAM) under control of a CPU (not shown) and when the CPU executes this program, the computer can be made to function as the time-series data analyzing apparatus according to an embodiment of the present invention. This computer includes an operating system which controls a variety of computer resources and provides graphical user interface (GUI) and the like.

A periodic health check data will be picked up as an example of multivariate time-series data D1 in the following description of the embodiment. The time-series data analyzing apparatus has an object of finding out an evident graph pattern indicating, for example, "composite factor time-series worsening the blood pressure" from the periodic health check data. Assume that a focused transitional pattern indicating the blood pressure worsening pattern has been specified for such a purpose. The minimum occurrence probability specified by a user preliminarily is assumed to be 0.5 and the minimum cause-and-effect strength is assumed to be 0.5. These focused transitional pattern and probability parameter and the like D8 are stored in the storage device preliminarily. How these values are utilized will be described later.

First, multivariate time-series data D1 stored in a memory medium or the like is fetched into the time-series data analyzing apparatus of this embodiment. The multivariate time-series data D1 refers to data of plural variables (for example, blood pressure, body fat, a result of inquiries about dietary habit), recorded with the time. The blood pressure is usually recorded as numeric and the result of inquiry about dietary habit is often recorded with an answer from three choices. The multivariate time-series data D1 may include a mixture of data of proportional scale and ordinal scale as long as a time (date and time) indicating when each data is recorded is accompanied.

The multivariate time-series data D1 fetched into the apparatus is discretized by the discretizing device 1. The "discretization" mentioned in this specification refers to abstraction of data according to a certain standard. For example, the blood pressure of an examined person whose blood pressure at the time of contraction is 130 to 140 can be abstracted using a term "normally high value". An example of the determination standard at the time of contraction is shown in FIG. 2. The numeric and standard values described here are just an example and different from the numeric and standard values used in actual operations. The discretizing device 1 discretizes data using a standard having such a threshold as required. For example, FIG. 4 shows a result of discretization of data shown in FIG. 3 based on the standard of FIG. 2. In the meantime, a case of using data abstracted to a sufficient level from the beginning like a result of dietary habit inquiry does not need the processing for discretization.

As a result of discretization of the multivariate time-series data D1 by the discretizing device 1, discrete time-series data including time and discretized data is output. The discrete time-series data refers to data stored in a health check database (not shown) and the like as shown in FIG. 4. Meanwhile, information which allows an individual to be specified like employee number is encrypted upon usage from viewpoints of individual information protection. As for determination of data, "G" is an abbreviation of green indicating "no problem", "Y" is an abbreviation of yellow, indicating "low level alarm" and "R" is an abbreviation of red, indicating "requires close examination" and as regards inquiry data, "G" means "no problem", "Y" means "slightly problematic" and "R" means "requires improvement". The time-series data mentioned here includes discrete quantitative time-series data having a standard such as health check data, quality control data, manufacturing process data.

The data dividing device 2 divides discrete time-series data output from the discretizing device 1 into pattern generation discrete time-series data D2 and pattern inspection discrete time-series data D3 containing no pattern generation discrete time-series data D2. These data are stored by some storage device in the computer.

The time-series event data generating device 3 collects the pattern generation discrete time-series data D2 for each employee, generates an item which is a combination of attribute name and attribute value in pair, arranges the items in ascending order of inspection years and generates an event from the item and inspection year. FIG. 5 shows an example of time-series event data D4. The "event" mentioned here refers to a proposition having a time stamp indicating when the item occurs. For example, an item "alcoholism risk Y" of examined person ID=1 means "the alcoholism risk in 2001 is at a slightly problematic level". Although the items are rearranged for each examined person, they may be arranged in time-series fashion about each product, individual and belonging department.

Next, the time-series event data generating device 3 provides the generated time-series event data D4 with an identifier (ID) and adds a correspondence with data ID in the discrete time-series data base D2 to a corresponding index (ID corresponding table D5). If any value is missing, no event is generated. A fact that there is a missing value indicates that the event did not happen. This apparatus can process data as it is if there is a lost value also.

Figure 6:
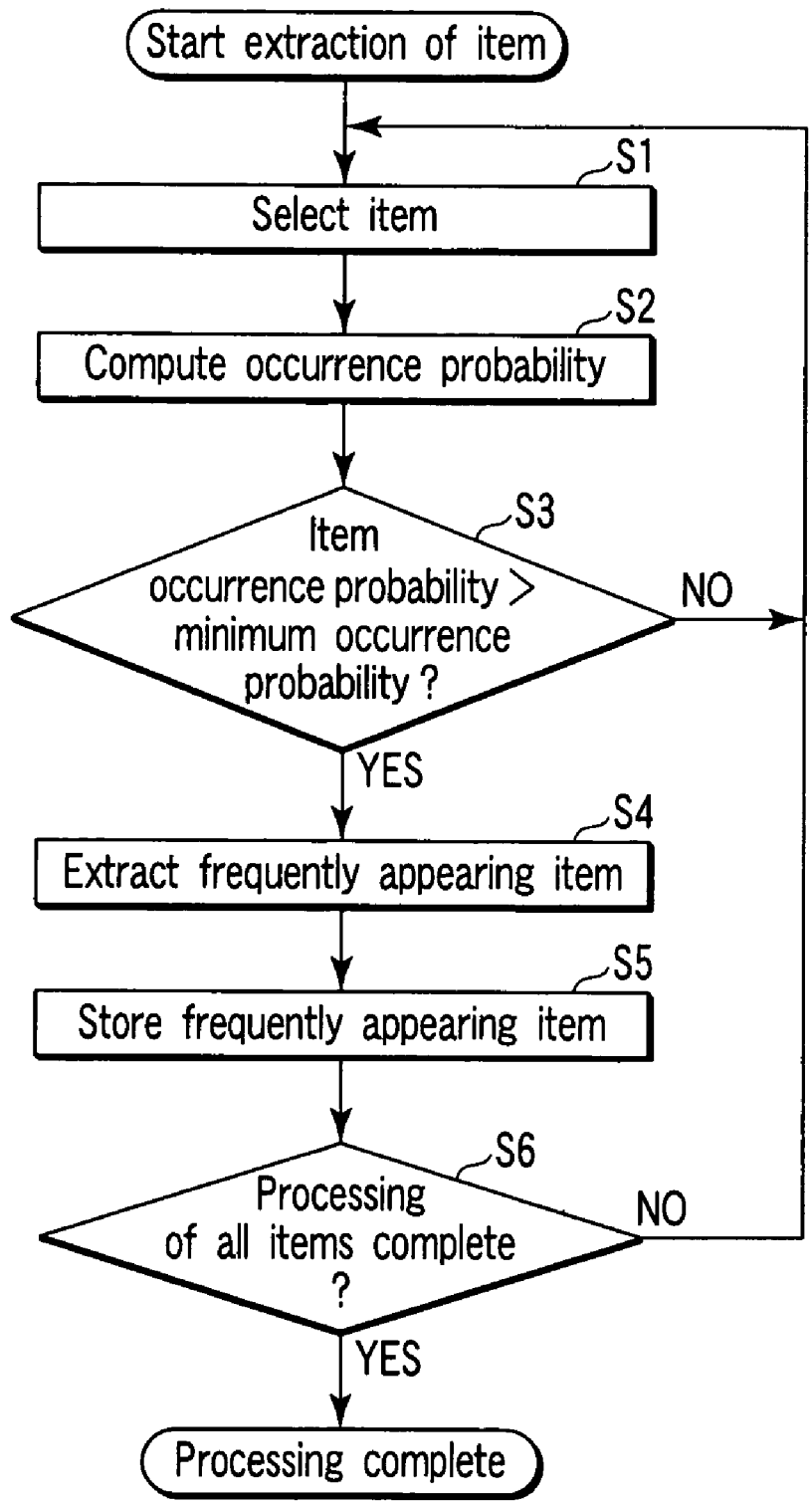
FIG. 6 is a flowchart showing the processing steps of a frequently appearing single item extracting device.

The frequently appearing single item extracting device 4 computes by what rate the single item occurs with respect to data of all examined persons and extracts only an item which exceeds the minimum occurrence probability specified by a user in advance. FIG. 6 is a flowchart showing the processing steps of the frequently appearing single item extracting device.

First, an item is selected (step S1) and the occurrence probability (item occurrence probability) of that item in data of all examined persons is computed (step S2). Whether or not this item occurrence probability exceeds a preliminarily determined minimum occurrence probability is determined (step S3). Unless the minimum occurrence probability is exceeded, the procedure returns to step S1 in which a next item is selected. If the minimum occurrence probability is exceeded, this item is extracted and stored as a frequently appearing item D6 (steps S4, S5). The processing described above is carried out to all items (step S6).

The items whose probability exceeds the minimum occurrence probability are called frequently appearing item. An example of the extracted item is shown in FIG. 7. For example, assume that the minimum occurrence probability specified by a user is 0.5. First, an occurrence probability of "dietary risk G" to all examined persons is computed. From the time-series event data D4 of FIG. 5, the examined person who has experienced "dietary risk G" once or more times is only an examined person 1 among three examined persons, i.e., only one person. Then, p (dietary risk G)=⅓ is the occurrence probability of "dietary risk G". This occurrence probability ⅓ is not evaluated to be frequently appearing because it is lower than the minimum occurrence probability. In this case, the "dietary risk G" is not a frequently appearing single item. On the other hand, the "dietary risk Y" is a frequently appearing single item because p (dietary risk Y) is ⅔ as a result of the same computation.

Figure 8:
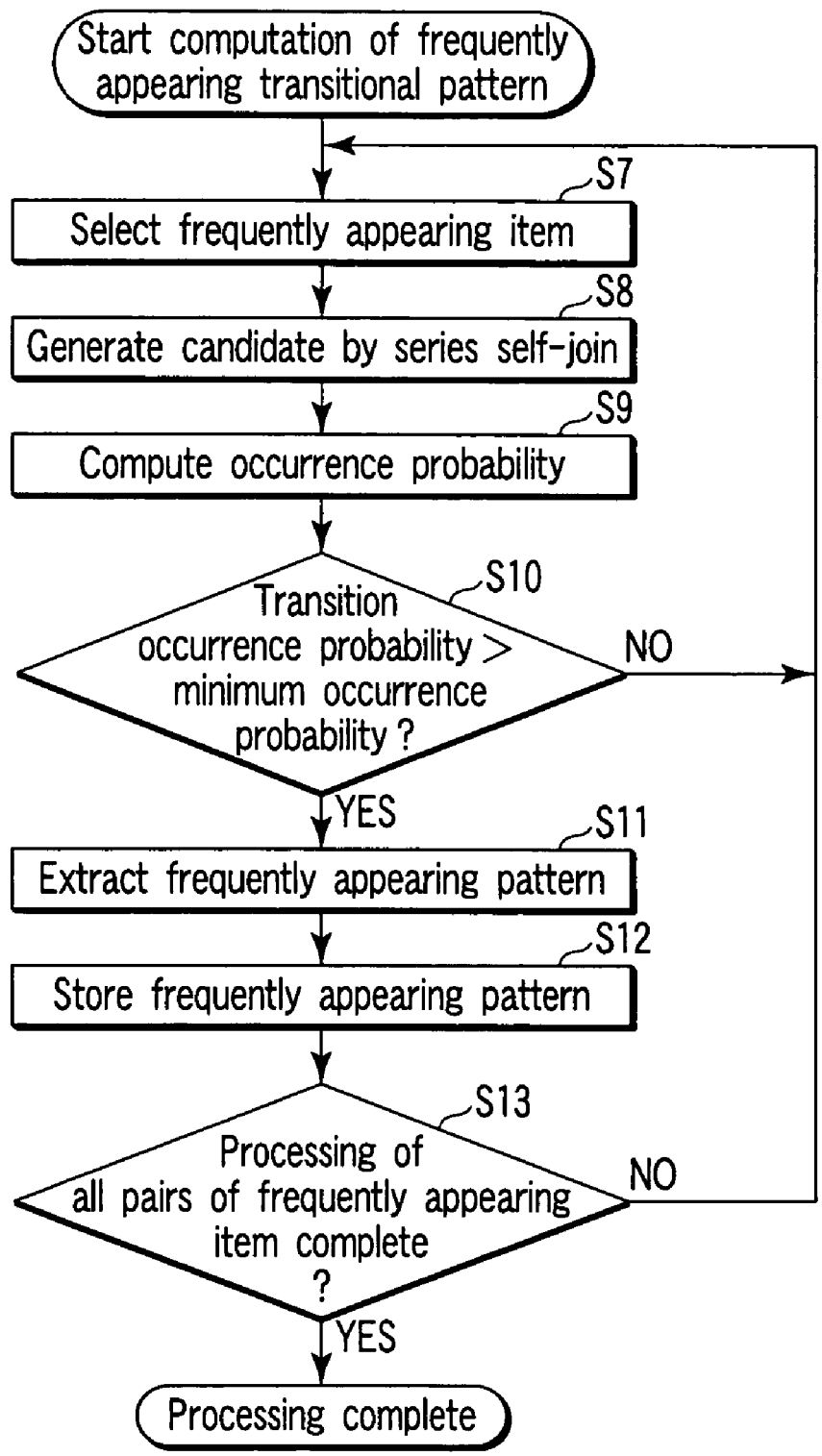
FIG. 8 is a flowchart showing the processing steps of frequently appearing single item transitional pattern generating device.

FIG. 8 is a flowchart showing the processing steps of the frequently appearing single item transitional pattern generating device.

The frequently appearing single item transitional pattern generating device 5 selects a frequently appearing item form the frequently appearing items (set) D6 extracted by the frequently appearing single item extracting device 4 and executes self-join upon that so as to generate a single item transitional pattern candidate (steps S7, S8). The self-join of the series refers to an operation of generating a transition series by multiplying the frequently appearing items in the frequently appearing item set D6. If a transitional pattern candidate is generated, the occurrence probability of each candidate in the time-series event data D4 and a set of examined persons ID falling under that pattern are computed and output with a candidate pattern (step S9).

FIG. 9 shows an example of generation of candidate pattern, computation of occurrence probability and result of computation processing of the examined persons ID falling under that pattern in determination of the blood pressure. Likewise, FIG. 10 shows an example of candidate generation of transitional pattern in dietary risk and FIG. 11 shows an example of candidate generation of the transitional pattern in alcoholism risk.

The frequently appearing single item transitional pattern generating device 5 extracts only the transitional patterns frequently appearing in the pattern generation time-series data D2 from an obtained transitional pattern candidate based on a determination by comparing the transition occurrence probability with the minimum occurrence probability (step S10) and outputs these as the frequently appearing transitional pattern D7 (steps S11, S12). A corresponding examined person ID is added to the frequently appearing transitional pattern D7. FIG. 12 shows an example of a result of the frequently appearing transitional pattern extraction.

The processing described above is carried out on all pairs of the frequently appearing items (step S13) and after plural frequently appearing transitional patterns are generated as a result thereof, the transitional pattern integrating device 6 integrates the frequently appearing transitional patterns with each other, computes a time lag between the transitional patterns by computing a time lag matrix and then generates frequently appearing integrated transitional pattern D9 taking into account the time lag.

FIG. 13 is a flowchart showing the processing steps of the transitional pattern integrating device. The transitional pattern integrating device 6 takes out two arbitrary patterns from the frequently appearing transitional pattern D7 (step S14) so as to compute a time lag matrix (step S15).

Figure 14:
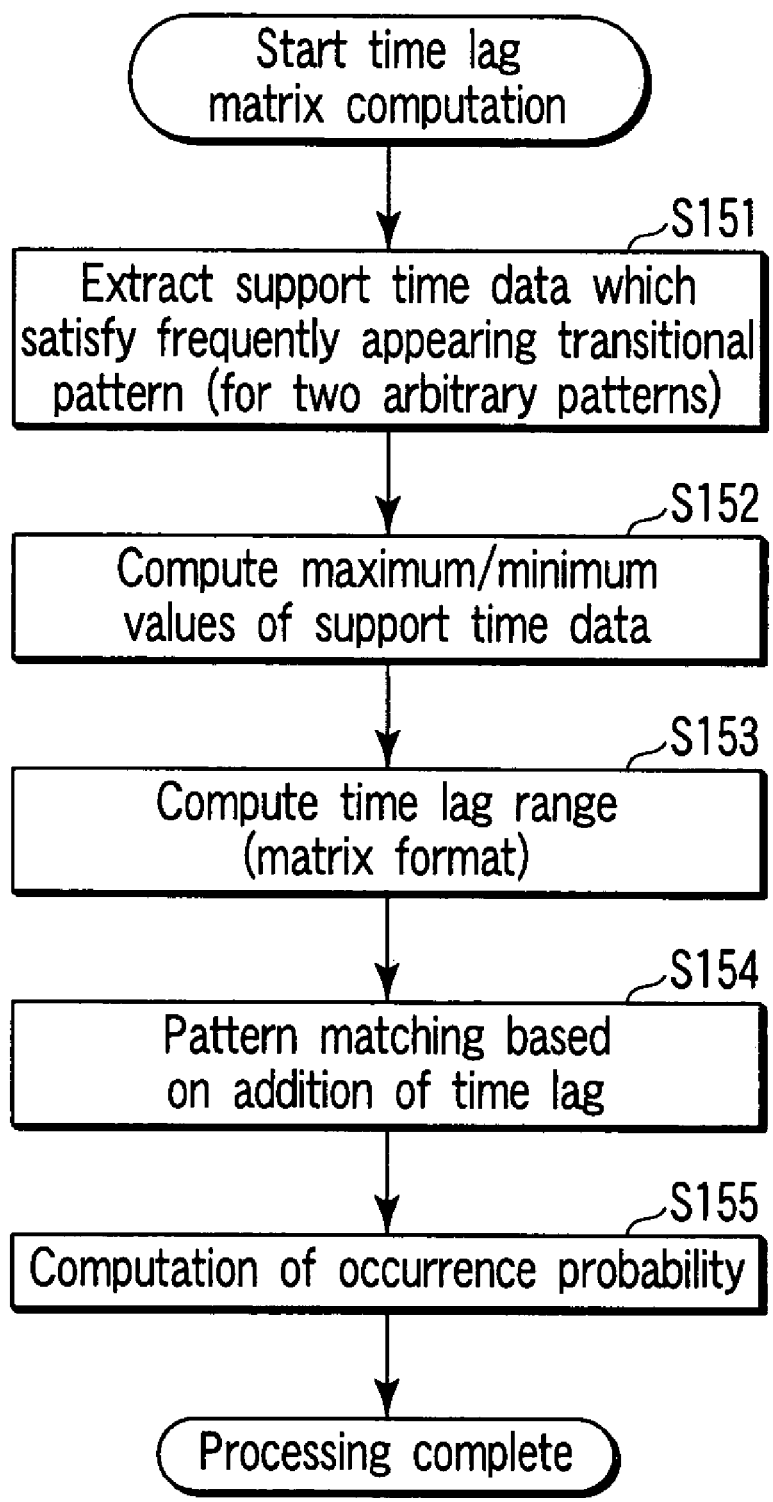
FIG. 14 is a flowchart showing the processing steps of a computing device for time lag matrix.

FIG. 14 is a flowchart showing the processing step of the time lag matrix computation. The time lag computing device 9 takes out a corresponding time-series data from the pattern generation discrete time-series data D2 according to a corresponding person ID of the arbitrary two frequently appearing transitional patterns so as to generate support time data (step S151). The support time data indicates a transition of time in the time-series event data of the corresponding person ID. For example, the examined person ID corresponding to "blood pressure check Y→blood pressure check R" in the frequently appearing transitional pattern in FIG. 12 is 1, 2, 3. FIG. 5 suggests that portions in which the examined person ID actually satisfies the "blood pressure check Y→blood pressure check R" in data 3 are three portions of from 2001 to 2002, from 2003 to 2004 and from 2001 to 2004. FIG. 15 shows an example of support time data of frequently appearing transitional pattern in blood pressure check. Similarly, FIG. 16 shows an example of support time data of dietary risk, and FIG. 17 shows an example of support time data of alcoholism risk.

After the support time data of all the frequently appearing patterns are obtained, a time lag is computed by subtracting a minimum value from a maximum value of each support time data and further subtracting 1. For example, in case of 2001→2003, it comes that 2003−2001−1=1 and the time lag is 1. By obtaining this about all the frequently appearing transitional patterns, their maximum values and minimum values are computed (step S152). Since according to this embodiment, 2001→2004 is a maximum range, it comes that 2004−2001−1=2. FIG. 18 shows a specific example of computation of the time lag range. This value means a maximum range of a time lag which may occur. Then, this time lag range is assumed to be ±2 and a value of time lag comprising −2, −1, ±0, +1, +2 is assumed to be a range of time lag matrix (step S153). Since the current series length of the frequently appearing transitional pattern is 2, two-dimensional time lag matrix is used. The time lag matrix can be increased in matrix dimension, for example, to three dimensions and four dimensions, if the series length is 3 or more. The format of a time lag matrix obtained as a result of the above computation is as shown in FIG. 19.

Figure 21:
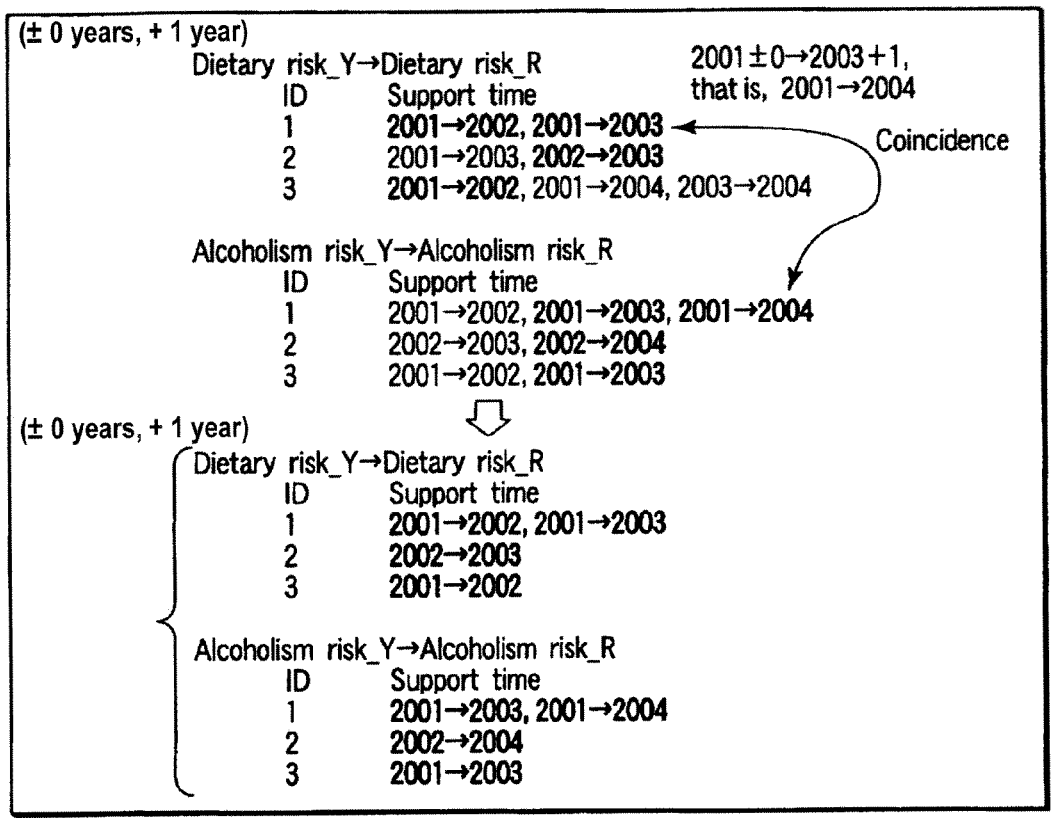
FIG. 21 is a diagram showing an example 1-2 of the pattern integration considering time lag.
Figures 22, 23:
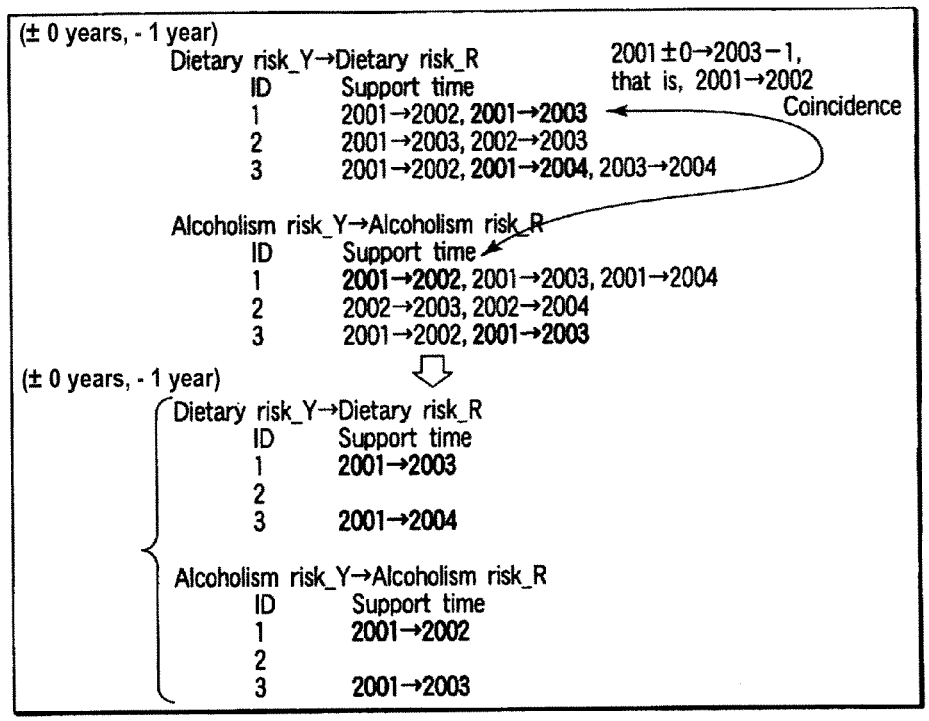
FIG. 22 is a diagram showing an example 1-3 of the pattern integration considering time lag.
FIG. 23 is a diagram showing an example 1 of time lag matrix computation.
Figures 24, 25:
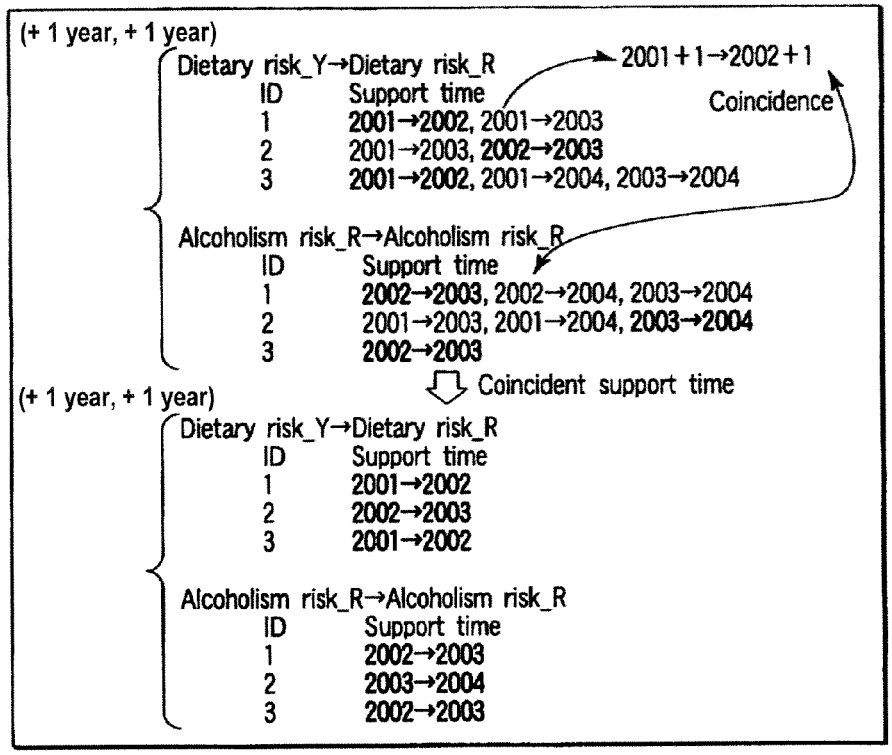
FIG. 24 is a diagram showing an example 2-1 of the pattern integration considering the time lag.
FIG. 25 is a diagram showing an example of the time lag matrix computation.

This time lag is added to one support time data of arbitrary two frequently appearing transitional patterns about all time lag combinations of this matrix based on the format of this time lag matrix and a frequency (occurrence probability) obtained by alignment of the support time data after added and adjusted (pattern matching) is recorded in a corresponding cell of time lag matrix (steps S154, S155). For example, in case of 2002→2003, it comes that 2003→2004 if time lag (+1 year, +1 year) may be added. However, in case of 2002→2003, time lags (+1 year, ±0 years) and (+1 year, −1 year) cannot be added. If they are added, it comes that 2003→2003 and 2003→2002 and the order of the time-series changes so that this is not a time-series transitional change. In this case, the support rate of a corresponding cell is set to 0%. FIGS. 20, 21, 22 show an example of integration of "dietary risk Y→dietary risk R" and "alcoholism risk Y→alcoholism risk R". FIG. 23 shows a time lag matrix obtained by integration of these patterns. FIG. 24 shows an example of integration of "dietary risk Y→dietary risk R" and "alcoholism risk R→alcoholism risk R". FIG. 25 shows a time lag matrix obtained by integration of these patterns.

When "dietary risk Y→dietary risk R" and "alcoholism risk Y→alcoholism risk R" are integrated from a time lag matrix of FIG. 23, it is determined that three time lags (±0 years, ±0 years), (±0 years, +1 year), (±0 years, −1 year) exceed the minimum occurrence probability (step S16 in FIG. 13). These integration patterns are patterns shown in FIGS. 20, 21, and 22. When "dietary risk Y→dietary risk R" and "alcoholism risk R→alcoholism risk R" are integrated, it is evident that only time lag (+1 year, +1 year) exceeds the minimum occurrence probability from the time lag matrix of FIG. 25. This integration pattern is a pattern shown in FIG. 24. The transitional pattern integrating device 6 stores these integrated patterns as the frequently appearing integrated transitional pattern D9 (step S18).

The transitional pattern integrating device 6 can integrate the frequently appearing integrated transitional pattern D9 with another new transitional pattern (for example, a focused transitional pattern). In this case, the transitional pattern integrating device 6 generates plural frequently appearing integrated transitional patterns by executing integration based on matching plural transitional patterns and the focused transitional patterns obtained by adding a time lag value selected within the time lag range to support time data of the frequently appearing integrated transitional pattern D9.

A purpose of the time-series data analyzing apparatus of this embodiment is to obtain a composite factor time-series pattern which worsens the blood pressure. When the focused transitional pattern is "blood pressure check Y→blood pressure check R" which worsens the blood pressure, a pattern indicating the relation between dietary risk and alcoholism risk can be obtained. This processing is made possible by integrating the previously obtained frequently appearing integrated transitional pattern D9 between dietary risk and alcoholisms risk and the blood pressure check frequently appearing transitional pattern D7 and obtaining a time lag matrix at the same time.

FIG. 26 shows an example of integration between the previously obtained frequently appearing integrated transitional pattern D9 between dietary risk and alcoholisms risk and the blood pressure check frequently appearing transitional pattern D7.

FIG. 26 indicates that (±0 years, ±0 years) and (−2 years, −2 years) are frequently appearing time lags by integration between the frequently appearing transitional pattern of the dietary/alcoholisms risk and the blood pressure check frequently appearing integrated transitional pattern. Each integration pattern candidate is generated from this result. When a pattern is generated by integrating the focused transitional pattern with other pattern, whether or not a time cause-and-effect-property is satisfied is inspected additionally (step S17). The time cause-and-effect property means a law that a cause always exists before an effect in time series. Whether or not an effect is generated is inspected after a cause appears in time series and then, when that pattern does not satisfy a prerequisite for a purpose of analysis, no pattern is established. Although, for example, in an integration pattern of (±0 years, ±0 years), blood pressure check and other factor are generated at the same time, other factor is generated after the blood pressure check in case of (−2 years, −2 years). In such a case, the integration is not established. FIGS. 27 and 28 show these examples. FIG. 29 shows an example that the integration is impossible.

If looking at the integration pattern generated in FIG. 28, the length of the integration pattern series is 4 by adding a time lag and integrating a pattern although the length of the series of each frequently appearing transitional pattern is 2. Although the length of individual pattern is small, a frequently appearing pattern having a long series can be obtained by adding a time lag and integrating patterns.

Figure 30:
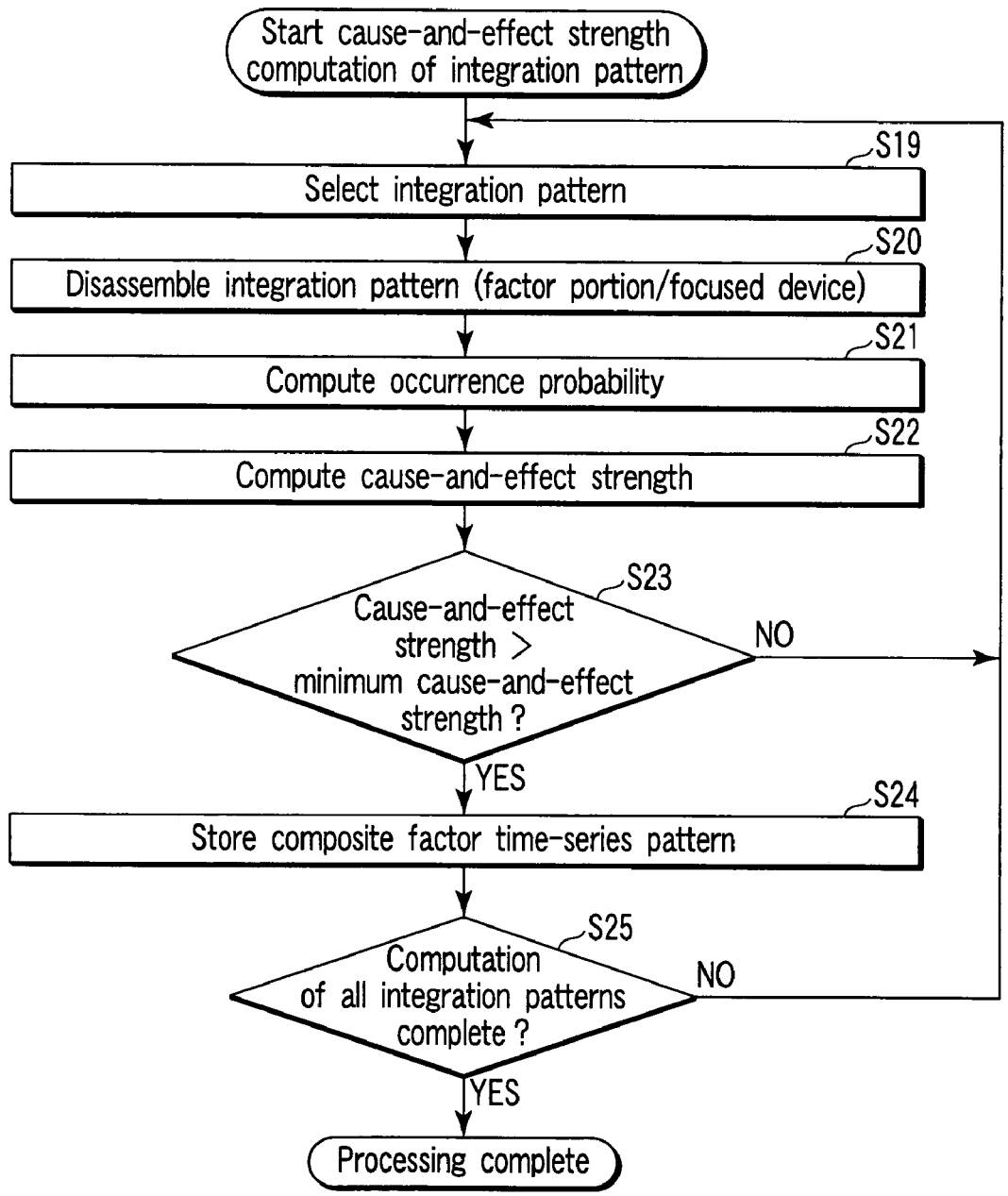
FIG. 30 is a flowchart showing the processing steps of a cause-and-effect strength computing device.

FIG. 30 is a flowchart showing the processing steps of the cause-and-effect strength computing device. The cause-and-effect computing device 7 computes a cause-and-effect strength to all of the frequently appearing integrated transitional patterns D9 obtained by the transitional pattern integrating device 6 using the pattern inspecting discrete time-series data D3. Only frequently appearing integrated transitional patterns which surpass the minimum cause-and-effect strength given as a probability parameter preliminarily are stored as the composite factor time-series pattern D10.

Figure 33:
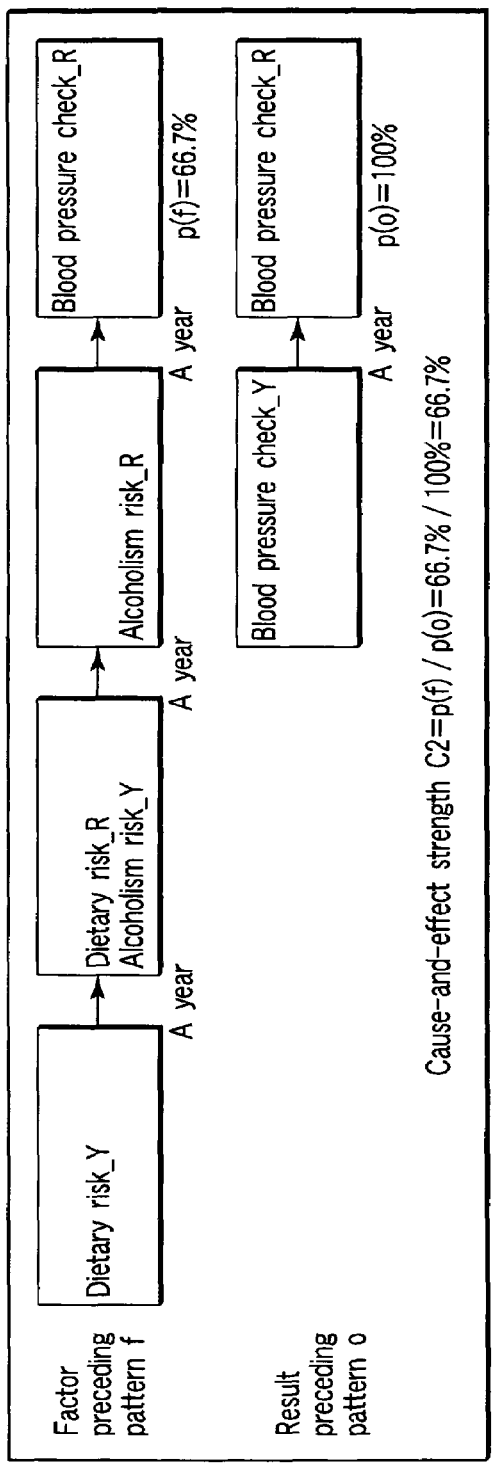
FIG. 33 is a diagram showing an example of the computation of the cause-and-effect strength.

First, an any frequently appearing integration pattern is picked out (step S19) and this integration pattern is disassembled to factor preceding pattern f and result preceding pattern o (step S20). Next, a factor preceding occurrence probability p (f) and a result preceding occurrence probability p (o) are computed using the pattern inspecting discrete time-series data D3 (step S21). A cause-and-effect strength C is computed from, for example, C=p (f)/p (o) based on this result (step S22). However, when p (o)=0, it is assumed that C=∞ and when p (f)=0, it is assumed that C=−∞. FIG. 31 shows an example of the pattern inspecting discrete time-series data D3. FIGS. 32, 33 show an example of computing an occurrence probability by picking out a cause portion from an integration pattern so as to compute a cause-and-effect strength. However, FIG. 32 shows an example of computation of the cause-and-effect strength of the frequently appearing integration pattern of FIG. 27 and FIG. 33 shows an example of computation of the cause-and-effect strength of the frequently appearing integration pattern of FIG. 28. FIG. 32 indicates that computed cause-and-effect intensities C1, C2 exceed the minimum cause-and-effect strength 0.5 that is given by a user. The cause-and-effect strength computing device 7 recognizes all the frequently appearing integration patterns exceeding the minimum cause-and-effect strength as a composite factor time-series pattern and stores them (steps S23, S24). The above-described processing is repeated for all the integration patterns (step S25). A time-series factor pattern having a long series can be found out by integrating plural transitional patterns using a time lag matrix. As described in a section about the time lag matrix computation as well as transitional pattern generation, a composite factor time-series having a long time axis can be found out by computation of the time lag matrix if the series of a single item transitional pattern is not 2 but 3 or more.

The display/operation device 8 displays a composite factor time-series pattern extracted by the process described above to a user through a display and receives an instruction from the user. At this time, the composite factor is rearranged so that the cause-and-effects are in the descending order. Consequently, the user can trace (display) the frequently appearing integrated transitional pattern D9, the frequently appearing transitional pattern D7, the frequently appearing item D6, the time-series event data D4, a corresponding examined person ID, the pattern generating discrete time-series data D2, the pattern inspecting discrete time-series data D3, and the multivariate time-series data D1 associated with the composite factor time-series pattern D10 by operating pattern indications on the screen as needed. The processing of the discretizing device 1 can be repeated by changing the focused transitional pattern and probability parameter D8. In case of repeated processing, data, ID table and patterns are left before repetition and a newly obtained data is added each time when the processing is repeated.

The first embodiment of the present invention as described above can extract a composite factor time-series pattern indicating a transition of composite factor from the multivariate time-series data. Therefore, composite factor accompanying a time passage can be specified from data.

Second Embodiment

In a time-series data analyzing apparatus of a second embodiment of the present invention, the cause-and-effect computing device 7 of the first embodiment inspects differences of averages of discrete quantitative values of an effect portion and analyzes variations of discrete time-series data which satisfy the cause portion in an event set of the composite factor pattern and picks up only data in which the difference is recognized as the composite factor time-series pattern.

Figure 34:
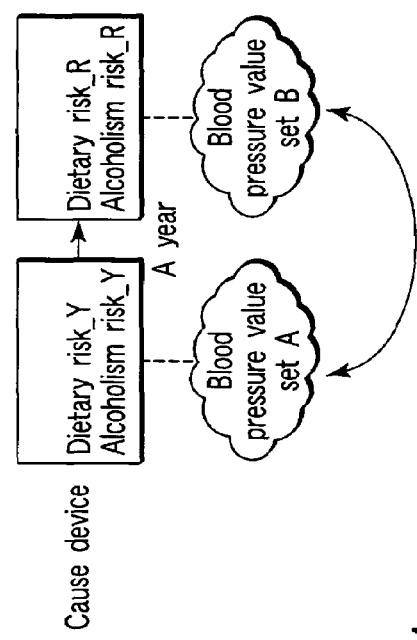
FIG. 34 is a diagram showing a pattern example and a frame for inspection.

FIG. 34 shows a pattern example and a framework for inspection. In this case, first, a set of corresponding examined person ID of the cause portion is picked out of the ID correspondence table D5 and a blood pressure value set A and a blood pressure value set B are picked out of the multivariate time-series data D1 using an examined person ID as a key. Next, whether the composite factor time-series of the cause portion raises or lowers the blood pressure is determined by inspecting a difference between averages of the blood pressure value set A and blood pressure value set B.

Third Embodiment

Figure 35:
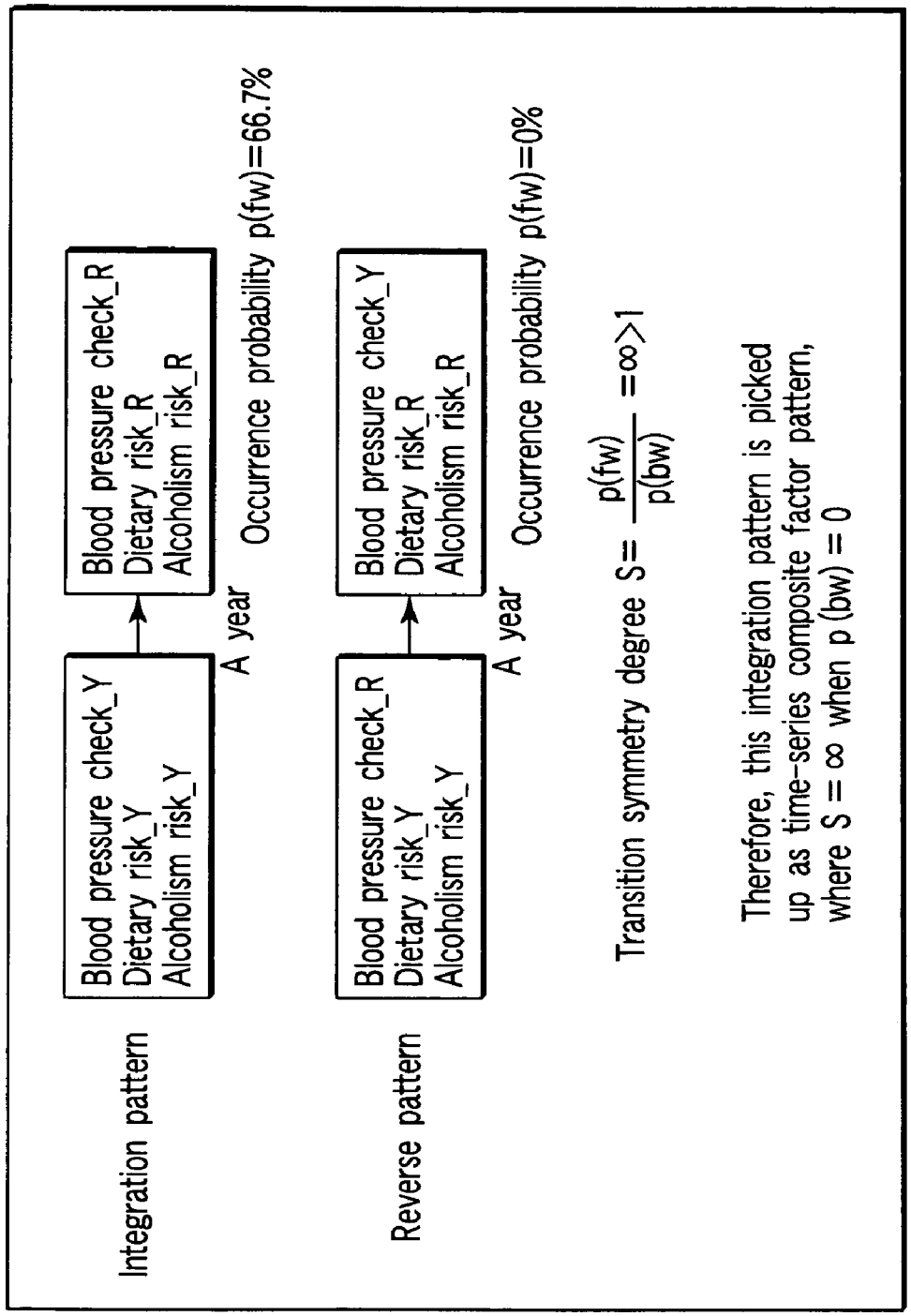
FIG. 35 is a diagram showing a computation example of the cause-and-effect strength based on the symmetry property of the transition.

In the time-series data analyzing apparatus of a third embodiment of the present invention, the cause-and-effect strength computing device 7 of the first embodiment determines differences of transitional symmetry property of the effect portion of the discrete time-series data which satisfy the cause portion in an event set of the composite factor pattern and picks up only data in which the difference is recognized as the composite factor time-series pattern. This embodiment can also be carried out by combining the second embodiment. The symmetry property of the transition mentioned here is a property indicating whether a criterion which is a ratio of occurrence probability between the composite factor time-series pattern D10 and a pattern in which data obtained by reversing the transitional direction of the effect portion is combined with the cause portion, that is, transitional symmetry degree S exceeds 1. Only an integration pattern having a feature can be found out as the composite factor time-series pattern D10 by examining the integration pattern according to the transitional symmetry degree. FIG. 35 shows an example of the pattern and a determination result. In this case, it is assumed that in case of p (o)=0, C=∞ and in case of p (f)=0, C=−∞.

If data needed by a user can be extracted locally by patternizing evident transition with a time passage from the time-series data regardless of the data being discrete quantitative or qualitative as described above, an appropriate transitional pattern can be grasped. Further, an embodiment of the present invention is useful when medical professionals such as industrial physician, hygienist and nurse design a health instruction content from a result of health check data analysis from viewpoints of improvement of work efficiency because labor and time for selecting and removing unnecessary information pieces can be omitted. Since a model can be established in process control in the same procedure as the health check data, a process administrator can grasp in what context of manufacturing process flow a fault occurs as an evident pattern. This is useful for building up a fault improvement plan for manufacturing process of products.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A time-series data analyzing apparatus which extracts a composite factor time-series pattern indicating a composite factor of a focused transitional pattern from time-series data, the apparatus comprising:

a dividing device configured to divide the time-series data to pattern generation time-series data and pattern inspection time-series data which do not include pattern generation time-series data;

a first generating device configured to generate a transitional pattern including a support time data indicating a transition of support time and having a transition occurrence probability higher than a minimum occurrence probability in the pattern generation time-series data;

a first computing device configured to compute a time lag range specified by a maximum value and a minimum value of support time in the support time data;

a second generating device configured to generate a plurality of frequently appearing integrated transitional patterns by executing integration based on pattern matching between a plurality of transitional patterns obtained by adding a time lag value selected within the time lag range to support time data of the transitional pattern and the focused transitional pattern;

a second computing device configured to compute cause-and-effect strength of each of the plurality of frequently appearing integrated transitional patterns using the pattern inspection time-series data; and a display device to display the composite factor time-series pattern having the cause-and-effect strength higher than the minimum cause-and-effect strength given preliminarily.

2. The time-series data analyzing apparatus according to claim 1, further comprising a discretizing device configured to discretize multivariate time-series data based on a preliminarily provided standard, the multivariate time-series data being included in the time-series data.

3. The time-series data analyzing apparatus according to claim 1, further comprising:
a second generating device configured to generate time-series event data from the pattern generation time-series data; and
an extracting device configured to extract a frequently appearing single item having an item occurrence probability higher than the minimum occurrence probability in the pattern generation time-series data from the time-series event data,
wherein the first generating device is configured to generate the transitional pattern based on a plurality of transitional pattern candidates obtained by self-joining of the frequently appearing single items.

4. The time-series data analyzing apparatus according to claim 1, further comprising:
an operation device to receive an instruction from a user, wherein the display device rearranges and displays the plurality of composite factor time-series patterns corresponding to the instruction.

5. The time-series data analyzing apparatus according to claim 1, further comprising:
an inspecting device configured to inspect whether each of the plurality of frequently appearing integrated transitional patterns satisfies time cause-and-effect property.

6. The time-series data analyzing apparatus according to claim 1, wherein the second computing device is configured to disassemble one of the plurality of frequently appearing integrated transitional patterns to a cause preceding pattern and a result receding pattern;
compute a cause preceding occurrence probability of the cause preceding pattern and an effect preceding occurrence probability of the result preceding pattern from the pattern inspection time-series data; and
wherein said cause-and-effect strength includes a ratio between the cause preceding occurrence probability and the effect preceding occurrence probability.

7. The time-series data analyzing apparatus according to claim 1, wherein the second computing device is configured to pick up only data in which a difference is recognized using statistical inspection of discrete quantitative value as said composite factor time-series pattern.

8. The time-series data analyzing apparatus according to claim 1, wherein the second computing device is configured to pick up only data in which a difference in symmetry property of transition is recognized as said composite factor time-series pattern.

9. A time-series data analyzing method for extracting a composite factor time-series pattern indicating a composite factor of a focused transitional pattern from time-series data, comprising:
dividing the time-series data to pattern generation time-series data and pattern inspection time-series data which do not include pattern generation time-series data;
generating a transitional pattern including a support time data indicating a transition of support time and having a transition occurrence probability higher than a minimum occurrence probability in the pattern generation time-series data;
computing a time lag range specified by a maximum value and a minimum value of support time in the support time data;
generating plurality of frequently appearing integrated transitional patterns by executing integration based on pattern matching between a plurality of transitional patterns obtained by adding a time lag value selected within the time lag range to support time data of the transitional pattern and the focused transitional pattern;
computing cause-and-effect strength of each of the plurality of frequently appearing integrated transitional patterns using the pattern inspection time-series data; and
displaying the composite factor time-series pattern having the cause-and-effect strength higher than the minimum cause-and-effect strength given preliminarily.

10. The time-series data analyzing method according to claim 9, further comprising discretizing multivariate time-series data based on a preliminarily provided standard, the multivariate time-series data being included in the time-series data.

11. The time-series data analyzing method according to claim 9, further comprising:
generating time-series event data from the pattern generation time-series data; and
extracting a frequently appearing single item having an item occurrence probability higher than the minimum occurrence probability in the pattern generation time-series data from the time-series event data, wherein the transitional pattern is generated based on a plurality of pattern candidates obtained by self-joining of the frequently appearing single items.

12. The time-series data analyzing method according to claim 9, further comprising:
receiving an instruction from a user, wherein the displaying includes rearranging and displaying the plurality of composite factor time-series patterns corresponding to the instruction.

13. The time-series data analyzing method according to claim 9, further comprising:
inspecting whether each of the plurality of frequently appearing integrated transitional patterns satisfies time cause-and-effect property.

14. The time-series data analyzing method according to claim 9, further comprising:
disassembling one of the plurality of frequently appearing integrated transitional patterns to a cause preceding pattern and a result preceding pattern; and
computing a cause preceding occurrence probability of the cause preceding pattern and an effect preceding occurrence probability of the result preceding pattern from the pattern inspection time-series data, wherein said cause-and-effect strength includes a ratio between the cause preceding occurrence probability and the effect preceding occurrence probability.

15. The time-series data analyzing method according to claim 9, wherein said composite factor time-series pattern includes data in which a difference is recognized using statistical inspection of discrete quantitative value.

16. The time-series data analyzing method according to claim 9, wherein said composite factor time-series pattern includes data in which a difference in symmetry property of transition is recognized.

* * * * *